United States Patent [19]

Holt et al.

[11] Patent Number: 5,001,291

[45] Date of Patent: Mar. 19, 1991

[54] HYDROCARBON DEHYDROGENATION REACTIONS

[75] Inventors: Andrew Holt, Bury, England; Paul C. J. Smith, Edinburgh, Scotland

[73] Assignee: BP Chemicals Limited, London, England

[21] Appl. No.: 329,817

[22] Filed: Mar. 28, 1989

[30] Foreign Application Priority Data

Mar. 31, 1988 [GB] United Kingdom ............... 8807732

[51] Int. Cl.$^5$ ............................................. C07C 1/00
[52] U.S. Cl. .................................................. 585/319
[58] Field of Search ............... 585/319, 324, 326, 441, 585/444, 659, 661

[56] References Cited

U.S. PATENT DOCUMENTS

| | | | |
|---|---|---|---|
| 3,839,225 | 10/1974 | Acres | 502/319 |
| 4,435,607 | 3/1984 | Imai | 585/444 |
| 4,565,898 | 1/1986 | O'Hara et al. | 585/319 |
| 4,652,687 | 3/1987 | Imai et al. | 585/444 |
| 4,691,071 | 9/1987 | Bricker | 585/319 |
| 4,717,779 | 1/1988 | Bricker et al. | 585/319 |

FOREIGN PATENT DOCUMENTS 0089183  9/1983  European Pat. Off. .

*Primary Examiner*—Patrick P. Garvin
*Assistant Examiner*—E. D. Irzinski
*Attorney, Agent, or Firm*—Brooks Haidt Haffner & Delahunty

[57] ABSTRACT

This invention relates to a process for (a) catalytically dehydrogenating a saturated hydrocarbon to the corresponding unsaturated hydrocarbon and hydrogen, (b) removing hydrogen from the products of step (a) over a catalyst supported on tin oxide and (c) dehydrogenating the products from step (b) under conditions of step (a). The process is effective for the production of e.g. styrene from ethylbenzene.

13 Claims, No Drawings

HYDROCARBON DEHYDROGENATION REACTIONS

The present invention relates to a method of improving hydrocarbon dehydrogenation reactions e.g. dehydrogenation of ethylbenzene to styrene.

In most hydrocarbon dehydrogenation reactions, one of the by-products of the reaction equilibrium is inevitably hydrogen. It is conventional in such reactions to use hydrogen abstractors to improve the yield and selectivity to the dehydrogenated product. For instance, GB 1308223 describes the use of carbon dioxide as hydrogen acceptor, whereas GB 1378151 describes the use of quinone, nitrobenzene and nitroparaffins for the same purpose.

It has also been suggested that the use of oxygen would help burn the hydrogen and some other by-products produced in the reaction thereby shifting the equilibrium in favour of the dehydrogenated products. However, the presence of free oxygen in the dehydrogenation reaction can lead to uncontrolled secondary oxidising reactions thereby enhancing the production of unwanted by-products and consequent loss of the desired dehydrogenated product. U.S. Pat. No. 4435607 describes the use of a multicomponent catalyst composited on a highly porous inorganic support such as alumina for the removal of hydrogen by oxidation with an oxygen-containing gas. The catalyst described in the above patent contains a Group VIII metal, a Group IVA metal (both present at up to 5 wt %) and a Group IA/IIA metal (up to 10 wt %) impregnated or co-precipitated on a highly porous inorganic support. However, the presence of a support such as alumina is detrimental to the process because it causes the cracking of a large amount of ethylbenzene and styrene to benzene and toluene by-products, which greatly reduces the selectivity of the process.

It is therefore an object of the present invention to mitigate these problems by carrying out the hydrogen removal in a stage separate from the dehydrogenation reaction stage.

It has now been found that by using as the hydrogen removal catalyst a Group VIII metal deposited on a tin oxide support, especially where the cracking of ethylbenzene and styrene to benzene and toluene by-products is greatly reduced thereby maintaining a high selectivity for the process.

Accordingly, the present invention is a process for the dehydrogenation of hydrocarbons, said process comprising at least three stages which consist essentially of (a) a first stage wherein the hydrocarbon is catalytically dehydrogenated at elevated temperature to a gaseous mixture comprising the dehydrogenated product and hydrogen, (b) a second stage wherein the gaseous mixture from the first stage is reacted at elevated temperature with oxygen or a gas containing molecular oxygen in the presence of a hydrogen removal catalyst comprising an oxide of one or more Group VIII metals selected from palladium, platinum, rhodium and ruthenium supported on an oxide of tin, wherein the support is present in an amount greater than 5% w/w of the total weight of catalyst and support, and (c) a third stage wherein the gaseous hydrocarbon mixture emerging from the second stage is dehydrogenated under the same conditions as in stage (a) above.

The hydrocarbons that may be catalytically dehydrogenated by this process include $C_2$–$C_{20}$ linear, branched or cyclic alkanes, alkenes, polyenes or alkyl aromatics. Thus alkanes can be dehydrogenated to olefins, cycloalkanes to cyclic olefins, olefins to diolefins and alkyl aromatics to vinyl aromatics. The process of the present invention is particularly suited to dehydrogenation reactions using a catalyst comprising iron oxide, preferably in the presence of steam. The iron oxide catalyst is preferably $Fe_3O_4$. This catalyst species can be derived by the reduction of commercially available $Fe_2O_3$ catalyst. The reduction of $Fe_2O_3$ can be carried out prior to use in the dehydrogenation step or 'in situ', for instance by conditioning over a duration in the dehydrogenation reactor where significant quantities of hydrogen are readily available for this purpose. A typical example of such a reaction is the dehydrogenation of alkylaromatic hydrocarbons to vinyl aromatic hydrocarbons, especially the dehydrogenation of ethylbenzene to styrene. GB-A-1176916 (Badger) describes this type of process.

The dehydrogenation of ethyl benzene to styrene is an endothermic reaction. It is therefore, conventional to supply this reaction with the necessary heat e.g. by mixing quantities of superheated steam with the hydrocarbon. The steam serves to maintain the selected dehydrogenation temperature, to prevent coke deposition on the catalyst used and to reduce the partial pressure of the reactants.

In the process of the present invention the dehydrogenation reaction is suitably carried out at a temperature from 500°–700° C., preferably from 600°–650° C. The dehydrogenation reaction is suitably carried out at a pressure ranging from 0.1 to 10 atmospheres, preferably from 0.1–1 atmosphere.

In the process the feed rate of steam to hydrocarbon on a weight basis is suitably from 1:1 to 10:1, preferably from 1:1 to 5:1.

In carrying out the catalytic dehydrogenation stage, e.g. using an iron oxide based catalyst, the liquid hourly space velocity (LHSV) based on the feed hydrocarbon may vary from 0.1–10 $hr^{-1}$, preferably from 0.1–2 $hr^{-1}$.

The gaseous mixture from the first stage is then passed onto a second stage. In this stage the gaseous mixture is brought into contact with a hydrogen removal catalyst in the presence of oxygen or a gas containing molecular oxygen.

The gas containing molecular oxygen is suitably air. The amount of oxygen or gas containing molecular oxygen introduced into this second stage may vary from 0.1:1 to 1:1 moles of oxygen per mole of hydrogen contained in the gaseous mixture emerging from the first stage, preferably from 0.4 to 0.6 moles of oxygen per mole of hydrogen. Within these ranges the amount of oxygen or gas containing molecular oxygen used should be such that all the oxygen fed is consumed in the hydrogen removal stage and no oxygen emerges from or is contained in the feed to the third stage. The amount of hydrogen in the gaseous mixture entering the second stage can be monitored by conventional sampling techniques.

The oxygen is suitably introduced into the second stage along with the gaseous mixture emerging from the first stage. The oxygen or the gas containing molecular oxygen is preferably introduced immediately prior to contact with a bed of the hydrogen removal catalyst.

The hydrogen removal catalyst in the second stage comprises an oxide of one or more Group VIII metals selected from palladium, platinum, rhodium and ruthenium supported on a tin oxide support. The metal oxide catalyst for this stage can be preformed e.g. by depositing the oxide(s) or a compound capable of giving rise to the respective oxide(s) on the tin oxide support followed by calcination in air at elevated temperature. Alternatively, the compound capable of giving rise to the oxide(s) can be deposited on the tin oxide support and the respective oxide(s) generated in situ in the hydrogen removal reactor where the catalyst is subjected to elevated temperatures in the presence of air. Examples of such compounds capable of giving rise to the metal oxides include metal salts and their complexes such as the chlorides, the nitrates, the sulphates and the amine chlorides of these metals. Palladium and platinum compounds are most preferred. Thus the palladium compound is suitably palladium nitrate. In the case of platinum the compound used is suitably chloroplatinic acid. Whichever compound(s) is/are used, they are deposited on a tin oxide support and then calcined at elevated temperature to form the respective metal oxide(s) on the tin oxide support. The Group VIII metal oxide is preferably that of palladium and/or platinum. The amount of Group VIII metal(s) in the hydrogen removal catalyst composition is suitably 0.01 to 20% by weight, preferably from 0.1 to 10% by weight based on the total catalyst inclusive of the support.

The amount of tin oxide support in the catalyst is greater than 5% w/w, suitably greater than 10% w/w, preferably at least 15% w/w based on the total weight of the catalyst and support.

The palladium tin oxide hydrogen removal catalyst may also be mixed with diluents which are inert under the reaction conditions such as MgO, CaO etc which reduce the total content of the Group VIII metal in the catalyst to a desired concentration. These inert diluents may be present at concentrations of up to 95 wt %.

The liquid hourly space velocity (LHSV) based on the hydrocarbon content of the gaseous mixture for this stage is the same as for stage (a) above.

The hydrogen removal catalyst for the second stage is suitably prepared by intimately mixing the Group VIII metal compound, e.g. the palladium nitrate and chloroplatinic acid with the tin oxide to form a homogeneous mixture which is then formed into a dough by kneading with a dilute acid e.g. nitric acid. The dough is then divided into smaller lumps and dried in an oven at elevated temperature in air e.g. at about 100°-120° C. for up to 24 hours. The dried catalyst is then calcined at elevated temperature, e.g. up to 350° C. in air for a duration until the metal compounds are transformed into the respective oxides. The calcined sample is then crushed, sieved and then pelletised e.g. with graphite or carbon.

The presence of oxygen enables the hydrogen in the gaseous reaction mixture from the first stage to be oxidised. This is an exothermic reaction and enables the temperature of the second stage catalyst to be maintained at the desired range. The second stage hydrogen removal catalyst comprising a Group VIII metal oxide supported on tin oxide is maintained at a temperature which is suitably from 300° to 700° C. preferably 500° to 700° C. at the time of contact with the gaseous reaction mixture from the first stage.

The gaseous mixture of hydrocarbons emerging from this second stage and substantially free from any oxygen or gas containing molecular oxygen is then fed into the third stage where the mixture is subjected to a further dehydrogenation.

The dehydrogenation conditions in this third stage are substantially similar to those employed in the first stage. In order to maximise the yield of desired dehydrogenated product, this third stage is essential. The resultant products from this third stage can be purified by conventional processes to recover the final dehydrogenated product.

The dehydrogenation process of the present invention has at least three stages at least two of which are dehydrogenation stages, but may be a multi-stage process suitably having in all 3-5 stages.

The process of the present invention can be operated batchwise or continuously.

The dehydrogenated products e.g. such as the vinyl aromatic hydrocarbon styrene are starting materials used in a variety of resins, plasticisers, elastomers, synthetic rubbers and the like.

The present invention is further illustrated with reference to the following examples.

A. CATALYST PREPARATION 269.0 gms of precipitated and dried tin oxide were mixed with 100 mls of 10% vol/vol nitric acid, prepared by diluting 100 mls concentrated nitric acid to 1000 mls with distilled water.

The mull of tin oxide was mixed for 15 minutes to homogenise in a Z blade mixer.

At the end of 15 minutes, 105 gms of a solution of palladium nitrate at 7.6% wt Pd content, were added slowly to the mixing tin oxide.

Mixing was continued for 30 minutes and then a solution of chloroplatinic acid—5.6 gms CPA at 5% wt Pt in 50 mls distilled water—was added to the mix. Mixing was continued for a further 30 minutes.

The mixed dough was then dried at 105° C. for 10 hrs and finally calcined in air to 350° C.

After calcination the lumps of oxide catalyst were crushed to 240 microns, mixed with 1% wt graphite and the powder pelleted into 4.8×4.8 mm cylinders.

B. CATALYTIC DEHYDROGENATION AND HYDROGEN REMOVAL

Reactor 1 (12" long and 1" I.D.) was charged with 100 grams (80 mls) of a commercial iron oxide catalyst (Girdler G64I), which was previously conditioned by operating in a styrene reactor for 3 days. The remaining space at the top of the reactor was filled with inert diluent in the form of cylindrical ceramic beads (4 mm×4 mm), which acted as a preheating zone.

Reactor 2 (18" long and 1" I.D.) incorporates the second and third stage reactors as Section 1 and Section 2 respectively. Section 1 was charged with 150 gms (85 mls) of the platinum oxide -palladium oxide-tin oxide catalyst prepared as in Section A above. The space at the top of Section 1 was filled with inert ceramic beads. Section 2 of this reactor was also charged with 100 grams (80 mls) of Girdler G64I iron oxide catalyst.

BRIEF DESCRIPTION OF THE DRAWINGS

FIG. 1 shows the experimental set-up used during the examples.

EXAMPLE 1

Nitrogen was fed to the two Reactors 1 and 2 at 6 l/hr while the two Reactors were brought up to 500° C. at atmospheric pressure. Water was then fed to the two Reactors at 70 g/hr. The temperature in Reactor 1 was then increased to 570° C. The temperature in Section 1 of Reactor 2 (containing the Pt, Pd/SnO₂ catalyst) was increased to 550° C., and the temperature in Section 2 (containing the iron oxide catalyst) was increased to 600° C. At this stage the nitrogen stream was switched off. Ethylbenzene of 99.6% purity was then fed to Reactor 1 at 40 g/hr and the reactor temperatures allowed to stabilise for 2 hours. Thus, Reactor 1 was at 570° C., Section 1 of Reactor 2 was at 550° C. and Section 2 of Reactor 2 was at 600° C. Air was then fed into Section 1 of Reactor 2 at a rate of 7 l/hr, and the system allowed to stabilise as previously for a further 2 hours. The product from Reactors 1 and 2 were sampled. The results are shown in Table 1.

Comparative Test 1 (Not According to the Invention)

This was carried out after a further 3 hours on stream. The conditions used were the same as Example 1, except no air was fed to the system.

EXAMPLE 2

This was carried out after a further 170 hours on stream. The conditions used were the same as Example 1.

Comparative Test 2 (Not According to the Invention)

This was carried out after a further 3 hours on stream. The conditions used were the same as Comparative Test 1.

EXAMPLE 3

A. CATALYST PREPARATION

Tin oxide powder was calcined in flowing air to 350° C./4 hours. 252.93 g of the powder was then slurried with 100 cm³ of 10%v/v HNO3 (aq) and the mixture stirred for 10 minutes. Tetramine palladium (11) nitrate (56.65 g of a 4.51% wt Pd solution) was added to the tin oxide slurry and stirred for 30 minutes. The slurry was then rotary evaporated to dryness and tray dried overnight at 105° C. The powder was then calcined in flowing air according to the following profile:
50°–150° C., 100° C./hr, hold 2 hours
150°–350° C., 100° C./hr, hold 2 hours
350°–600° C., 100° C./hr, hold 4 hours The powder was then mixed with 1% wt graphite and pelleted.

B. CATALYTIC DEHYDROGENATION AND HYDROGEN REMOVAL

The reactors were set up as in Example 1 except that section 1 of reactor 2 was charged with 100 g (56 ml) of the palladium oxide-tin oxide catalyst prepared as in Section A above. The experimental conditions and product analyses are shown in Table 1.

Comparative Test 3 (Not According to the Invention)

The reactors were set up as in Example 3 above except that the palladium oxide-tin oxide catalyst had been removed from Section 1 of reactor 2 and replaced with inert ceramic beads. The reactors were commissioned as in Example 1 above, except that there was no air flow to the reactors. The temperature of the reactors were the same as for Example 3 above.

EXAMPLE 4

A. CATALYST PREPARATION

Tin oxide powder was calcined in flowing air to 350° C./4 hours. 250.48 g of the powder was then slurried with 100 cm³ of 10% v/v HNO3 (aq) and the mixture stirred for 10 minutes. Tetramine palladium (11) nitrate (27.94 g of a 4.51% wt Pd solution) was added to the tin oxide slurry and stirred for 30 minutes. The slurry was then rotary evaporated to dryness and tray dried overnight at 105° C. The powder was then calcined in flowing air according to the following profile:
50°–150° C., 100° C./hr, hold 2 hours
150°–350° C., 100° C./hr, hold 2 hours
350°–600° C., 100° C./hr, hold 4 hours The powder was then mixed with 1% wt graphite and pelleted.

B. CATALYTIC DEHYDROGENATION AND HYDROGEN REMOVAL

The reactors were set up as in Example 1 except that Section 1 of reactor 2 was charged with 45 gms (25 mls) of the palladium oxide-tin oxide catalyst prepared as in Section A above. The experimental conditions and product analyses are shown in Table 1.

Comparative Test 4 (Not According to the Invention)

This was carried out approximately 6 hours after CT 3. The conditions used were the same as CT3 except that the temperature in Section 2 of reactor 2 was increased to 620° C.

EXAMPLE 5

After completion of Example 4 the temperature of Section 1 of reactor 2 was reduced to 550° C. with all other conditions remaining constant. The product from reactors 1 and 2 were sampled after approximately a 3 hour period. The benefit of the increased styrene yield is evident when compared against Comparative Test 4.

EXAMPLE 6

A. CATALYST PREPARATION (a) 50 mls of 10 wt % nitric acid was added to 100 g of tin oxide and a small amount of distilled water was added to make a thick paste.

(b) 20 g of palladium tetramine chloride solution (containing 10.76% w/w Pd) was added to the mull of tin oxide, and the mixture was stirred for about 15 minutes.

(c) The catalyst was dried slowly in a rotavapor under vaccum at approximately 60° C. for approximately 2–3 hours, followed by oven drying for 8 hours at 100° C.

(d) The catalyst was calcined in air for 6 hours at 500° C., after which it was crushed to <325 micrometers.

(e) 50 g of the crushed catalyst was mixed thoroughly with 150 g of MgO powder, after which the catalyst was pelleted into 3.3×4.9 mm cylinders.

B. CATALYTIC DEHYDROGENATION AND HYDROGEN REMOVAL

The reactors were set up as in Example 1 except that Section 1 of reactor 2 was charged with 100 gms (80 mls) of the palladium oxide-tin oxide-magnesium oxide catalyst prepared as in Section A above. The experimental conditions and product analyses are shown in Table 1. The benefit of the increased styrene yield is evident when compared against Comparative Test 4.

EXAMPLE 7

A. CATALYST PREPARATION 25 g of the catalyst synthesised in steps (a)-(d) of Example 6, were added to 175 g of MgO powder, after which the catalyst was pelleted into 2.5×3.9 mm cylinders.

B. CATALYTIC DEHYDROGENATION AND HYDROGEN REMOVAL

The reactors were set up as in Example 1 except that Section 1 of reactor 2 was charged with 88 gms (77 mls) of the palladium oxide-tin oxide-magnesium oxide catalyst prepared as in Section A above. The experimental conditions and product analyses are shown in Table 1. The benefit of the increased styrene yield is evident when compared against Comparative Test 4.

EXAMPLE 8

This example demonstrates the very low formation of benzene and toluene by-products using tin oxide support catalysts for selective $H_2$ removal compared with an alumina supported catalyst typical of that described in U.S. Pat. No. 4435607.

A. CATALYST PREPARATION

The tin oxide supported catalyst used was the same as that used in Example 4.

B. CATALYTIC DEHYDROGENATION AND HYDROGEN REMOVAL

The reactors were set up as in Example 1 except that Section 1 of reactor 2 was charged with 100 gms (58 mls) of the palladium oxide-tin oxide catalyst prepared as in Section A above. In addition, there was no iron oxide dehydrogenation catalyst present in Section 2 of reactor 2. The experimental conditions and product analyses are shown in Table 1.

Comparative Test 5 (Not According to the Invention)

A. CATALYST PREPARATION

This catalyst, containing 0.5% Pd on gamma-alumina, was purchased ready made from United Catalysts Inc. Its surface area was 206 m²/g, which is within the range of surface areas described in U.S. Pat. No. 4435607.

B. CATALYTIC DEHYDROGENATION AND HYDROGEN REMOVAL

The reactors were set up as in Example 8 above except that 40 gms (50 mls) of the palladium oxide-alumina catalyst was charged to Section 1 of reactor 2 in place of the palladium oxide-tin oxide catalyst. The experimental conditions and product analyses are shown in Table 1. The results clearly show the much higher formation of benzene and toluene by-products when using the alumina-supported catalyst compared with the tin oxide supported catalyst.

TABLE

| Example No. | Temperature °C. Reactor 1 | Reactor 2 Section 1 | Reactor 2 Section 2 | Air Flow to Reactor 2 l/hr | Product Formation in Reactors (wt %) Reactor 1 | | | | Reactor 2 | | | | Hydrogen Removed % |
|---|---|---|---|---|---|---|---|---|---|---|---|---|---|
| | | | | | Benzene | Toluene | EB | Styrene | Benzene | Toluene | EB | Stryene | |
| 1 | 570 | 550 | 600 | 7.0 | 0.3 | —* | 50.9 | 48.6 | 1.1 | 1.3 | 20.8 | 76.5 | —* |
| CT 1 | 570 | 550 | 600 | 0 | —* | —* | 53.4 | 46.5 | 1.2 | 3.2 | 27.4 | 68.1 | N/A |
| 2 | 570 | 550 | 600 | 7.0 | 0.4 | 1.0 | 51.9 | 46.7 | 1.1 | 2.3 | 20.0 | 76.3 | —* |
| CT 2 | 570 | 550 | 600 | 0 | 0.3 | 0.7 | 51.4 | 47.5 | 1.0 | 3.5 | 25.1 | 70.2 | N/A |
| 3 | 550 | 600 | 600 | 8.4 | 0.5 | 1.0 | 61.0 | 37.3 | 1.2 | 3.3 | 25.6 | 69.6 | 61.8 |
| CT 3 | 550 | — | 600 | 0 | 0.7 | 1.1 | 58.2 | 39.7 | 1.0 | 2.6 | 31.5 | 64.8 | N/A |
| 4 | 550 | 600 | 620 | 8.4 | 0.6 | 1.0 | 60.1 | 38.1 | 1.3 | 4.2 | 16.5 | 77.7 | 100 |
| CT 4 | 550 | — | 620 | 0 | 0.7 | 1.1 | 58.2 | 39.7 | 1.3 | 3.8 | 23.1 | 71.6 | N/A |
| 5 | 550 | 550 | 620 | 8.4 | 0.6 | 1.2 | 57.4 | 40.7 | 1.4 | 4.3 | 15.4 | 78.6 | 85.3 |
| 6 | 550 | 600 | 600 | 9.0 | 0.5 | 1.0 | 60.9 | 37.4 | 1.3 | 3.0 | 26.6 | 68.8 | 100 |
| 7 | 550 | 600 | 620 | 9.0 | 0.5 | 1.0 | 60.8 | 37.5 | 1.4 | 3.9 | 20.1 | 74.4 | 100 |
| 8 | 550 | 517 | — | 9.0 | 0.7 | 1.1 | 59.9 | 38.1 | 1.2 | 1.3 | 57.2 | 39.6 | 91.6 |
| CT 5 | 550 | 517 | — | 8.0 | 0.2 | 0.9 | 52.8 | 46.1 | 13.3 | 4.7 | 63.1 | 18.7 | —+ |

*Analysis unavailable due to faulty analyser
CT = Comparative Test
EB = Ethylbenzene
+not possible to determine the % hydrogen removed due to the very large excess of cracking to benzene and toluene, which produces large amounts of hydrogen

We claim:
1. A process for the dehydrogenation of hydrocarbons, said process comprising at least three stages which consist essentially of
   (a) a first stage wherein the hydrocarbon is catalytically dehydrogenated at elevated temperature to a gaseous mixture comprising the dehydrogenated product and hydrogen,
   (b) a second stage wherein the gaseous mixture from the first stage is reacted at elevated temperature with oxygen or a gas containing molecular oxygen in the presence of a hydrogen removal catalyst comprising an oxide of one or more Group VIII metals selected from palladium, platinum, rhodium and ruthenium supported on an oxide of tin, wherein the support is present in an amount greater than 5% w/w of the total weight of catalyst and support, and
   (c) a third stage wherein the gaseous hydrocarbon mixture emerging from the second stage is dehydrogenated under the same conditions as in stage (a) above.

2. A process according to claim 1 wherein the hydrocarbon is a $C_2$-$C_{20}$ linear, branched or cyclic alkane, alkene, polyene or alkyl aromatic.

3. A process according to claim 1 wherein the hydrocarbon is ethyl benzene which is dehydrogenated to styrene.

4. A process according to claim 1 wherein the dehydrogenation catalyst for stage (a) comprises iron oxide.

5. A process according to claim 1 wherein the dehydrogenation catalyst for state (a) is $Fe_3O_4$ derived from $Fe_2O_3$ in situ during the dehydrogenation reaction.

6. A process according to claim 1 wherein the dehydrogenation stage (a) is carried out in the presence of steam.

7. A process according to claim 1 wherein the dehydrogenation stage (a) is carried out at a temperature from 500°–700° C. and a pressure of 0.1 to 10 atmospheres.

8. A process according to claim 4 wherein the LHSV for the hydrocarbon feed based on the iron oxide catalyst is from $0.1\text{-}10hr^{-1}$.

9. A process according to claim 1 wherein the gaseous mixture emerging from stage (a) is brought into contact with a hydrogen removal catalyst comprising one or more Group VIII metal oxides supported on tin oxide in step (b) whereby the metal oxide is generated in situ from a compound capable of giving rise to the metal oxide under the reaction conditions.

10. A process according to claim 1 wherein the hydrogen removal catalyst contains a diluent which is inert under the reaction conditions.

11. A process according to claim 1 wherein the amount of oxygen or gas containing molecular oxygen introduced into stage (b) varies from 0.1:1 to 1:1 moles of oxygen per mole of hydrogen contained in the gaseous mixture emerging from stage (a).

12. A process according to claim 1 wherein the hydrogen removal catalyst is maintained at a temperature from 300°–700° C. during stage (b).

13. A process according to claim 1 wherein the gaseous mixture emerging from stage (b) is substantially freed of oxygen or gases containing molecular oxygen prior to dehydrogenation in stage (c).

* * * * *

UNITED STATES PATENT AND TRADEMARK OFFICE
CERTIFICATE OF CORRECTION

PATENT NO. : 5,001,291

DATED : March 19, 1991

INVENTOR(S) : Andrew Holt, et al

It is certified that error appears in the above-identified patent and that said Letters Patent is hereby corrected as shown below:

Col. 2, l. 41, should read "from $--0.1-10hr^{-1}--$.

Claim 8, line 3, should read $--0.1-10hr^{-1}--$.

Signed and Sealed this

Tenth Day of November, 1992

*Attest:*

DOUGLAS B. COMER

*Attesting Officer*      *Acting Commissioner of Patents and Trademarks*